United States Patent [19]

Montecalvo et al.

[11] Patent Number: 5,205,297
[45] Date of Patent: Apr. 27, 1993

[54] MULTIPURPOSE MEDICAL STIMULATION ELECTRODE

[75] Inventors: David A. Montecalvo, Eden Prairie; David Rolf, Minneapolis, both of Minn.

[73] Assignee: LecTec Corporation, Minnetonka, Minn.

[21] Appl. No.: 344,698

[22] Filed: Apr. 28, 1989

Related U.S. Application Data

[63] Continuation-in-part of Ser. No. 173,589, Mar. 25, 1988, abandoned.

[51] Int. Cl.$^5$ ............................................. A61N 1/18
[52] U.S. Cl. ............................ 128/798; 128/639; 128/640; 128/641; 128/802; 252/500; 522/79; 522/86; 522/152
[58] Field of Search ............... 128/639–641, 128/798, 802–803; 604/20; 252/500; 522/79, 86, 152

[56] References Cited

U.S. PATENT DOCUMENTS

| | | |
|---|---|---|
| 4,270,832 | 6/1981 | Tanabe .................... 339/105 |
| 4,274,420 | 6/1981 | Hymes .................. 128/798 X |
| 4,301,805 | 11/1981 | Trevarton ............... 128/419 P |
| 4,349,030 | 9/1982 | Belgard ................. 128/419 PG |
| 4,458,696 | 7/1984 | Larimore .................. 128/798 |
| 4,474,570 | 10/1984 | Ariura et al. .............. 128/798 X |
| 4,539,996 | 9/1985 | Engel ..................... 128/798 X |
| 4,577,643 | 3/1986 | Beranek .................. 128/785 |
| 4,674,512 | 6/1987 | Rolf ....................... 128/640 |
| 4,675,009 | 6/1987 | Hymes ..................... 604/304 |
| 4,699,146 | 10/1987 | Sieverding ............... 128/798 X |
| 4,706,680 | 11/1987 | Keusch ................... 128/798 X |
| 4,717,378 | 1/1988 | Perrault .................. 128/639 X |

FOREIGN PATENT DOCUMENTS

| | | | |
|---|---|---|---|
| 8100785 | 3/1981 | PCT Int'l Appl. ........... 128/798 |
| 2045088 | 10/1980 | United Kingdom ............ 128/798 |

*Primary Examiner*—Kyle L. Howell
*Assistant Examiner*—Brian L. Casler
*Attorney, Agent, or Firm*—James V. Harmon

[57] ABSTRACT

A multipurpose medical stimulating electrode is described for use in external cardiac pacing, Transcutaneous Electrical Nerve Stimulation and neuromuscular stimulation which includes a protective cover layer at the top extending over and bonded to the upper surface of an electrically conductive layer, e.g. carbon filled silicone rubber having a resistivity of about 100 ohm centimeters on the lower surface of which is coated a selfsupporting skin contacting hydrogel layer comprising a matrix having a sticky surface adapted to make a good electrical contact with the skin and having a resistivity of greater than 1,000 and less than 10,000 ohm centimeters. The matrix is composed of natural or synthetic hydrocolloid, e.g. polyacrylamide, and/or natural gum such as karaya gum, water and a humectant comprising a polyhydric alcohol and optionally with $Mg(OAc)_2$ as a gelation inhibitor and electrolyte.

12 Claims, 2 Drawing Sheets

MULTIPURPOSE MEDICAL STIMULATION ELECTRODE

This is a continuation-in-part of an application having the same title, Ser. No. 173,589, filed Mar. 25, 1988, now abandoned.

FIELD OF THE INVENTION

The present invention relates to medical electrodes and more particularly to an externally applied multipurpose stimulation electrode.

BACKGROUND OF THE INVENTION

External cardiac pacing utilizes relatively high and therefore potentially painful DC current (10–100 mA). This is required to achieve effective stimulation of cardiac muscle located deep within the chest. To deal with these and other problems, various external stimulating electrodes have been previously proposed for medical purposes. For example, U.S. Pat. No. 4,349,030 describes an electrode used for external cardiac pacing which includes as a skin contacting electrically conducting member a porous sponge formed from cellulose in which is absorbed an electrically conductive fluid. Electrical conductivity of the fluid provides a uniform current density to reduce stimulation of local sensory nerves. For example, a ¼ inch thick cellulose sponge or a piece of gauze is dampened prior to use with tap water or a weak electrolyte. A fluid-like gel can also be used to saturate the sponge or gauze. In order to be absorbed into the fibrous material the gel must have fluid consistency. The sponge is connected to an electrically conductive metal backing having an insulated wire permanently attached to it. In commercial equipment utilizing the patented structure, a male plug is connected to the free end of the insulated wire. During use, the male plug connects to a female receptor located in the external cardiac pacing device or power supply. Other commercially available external cardiac pacing electrodes used in conjunction with specified external cardiac electrical pacing devices are also manufactured with permanent wiring having a wire for supplying current with a unique male plug at its free end that is adapted to connect to a complementary female receptor located in the external pacing equipment.

These prior electrodes suffer from several important shortcomings. First, they can only be used with specific electrical pacing equipment because the male plugs wired in place permanently will only fit a specific piece of equipment. Second, the construction of the electrode makes it relatively expensive because of its size and bulk. Moreover, the electrolyte applied to the sponge must necessarily be in a fluid state to flow into the pores of the sponge or gauze supporting it. Its fluidity however allows the electrolyte to smear, run or leave residue on the patient's body, as well as drying out on the shelf.

U.S. Pat. No. 4,274,420 describes a monitoring and stimulation electrode. The broad statement is made that the resistivity can be anything less than 10,000 ohms-meter (i.e. less than 1,000,000 ohms-centimeter), but the preferred resistivity is less than 1,000 ohms-meter or 100,000 ohms-centimeter. While the patent does disclose a broad range for the purpose of showing that the resistivity is not unduly restrictive, it does not instruct or direct one to a useful level of resistivity employed in accordance with the present invention. Throughout the patent, it is emphasized that there is an advantage in using low AC resistivity in electrodes, e.g. column 3, lines 20–26; column 4, lines 31–32; and example 20, lines 15–20. This is consistent with teachings elsewhere in the patent which suggest the use of relatively large quantities of strongly ionized electrolytes such as sodium chloride. Thus, although the suggestion is made that the electrode can be used for stimulation purposes, there is no disclosure of how one can achieve a painless heart stimulation using constant current, i.e. DC current.

Other stimulating electrodes used for Transcutaneous Electrical Nerve Stimulation (TENS) and neuromuscular stimulation (NMS) utilize a conductive adhesive and a conductive rubber backing. TENS typically employs AC electricity at about 10 mAmp current levels. Because of the alternating nature of this current it generally is considered less painful and irritating than comparable DC levels. One design application of these electrodes, NMS, typically employs DC electricity at about 10 mAmp current levels. This is more similar to cardiac pacing than TENS yet operates at much lower current levels and therefore has much less potential for pain generation than cardiac pacing. Ordinary electrodes, however, do not provide optimal results for painless cardiac stimulation, in part because the electrically conductive matrix will allow current to concentrate in areas of lower impedance occurring in the skin surface. This can occur progressively as the patient is stimulated, causing a runaway condition in which the skin of the patient may even break down electrically, allowing a substantial surge of current to flow through a localized area, causing extreme pain to the patient. Moreover, although conventional TENS and NMS electrodes may provide comfortable stimulation in their designed purpose, both of these electrodes are single purpose electrodes unsuited for cardiac pacing applications due to their relatively high conductivity.

| Typical Applied Current Levels for Various Stimulation Applications | |
|---|---|
| Transcutaneous Nerve Stimulation | 1–10 mA (AC) |
| External Cardiac Pacing | 10–60 mA (DC) |
| Neuro-Muscular Stimulation (NMS) | 1–40 mA (DC) |

In view of these and other deficiencies of the prior art, it is a general object of the invention to provide a multipurpose medical electrode suited for Transcutaneous Electrical Nerve Stimulation, neuromuscular stimulation and for cardiac pacing with a provision for reliably preventing current build-up in localized areas and a runaway condition in which a surge of current passes through a localized area of the skin where electrical resistance is broken down under certain applied current loads. A further object is to provide an electrode wherein the electrically conductive skin-contacting matrix is a stable, semi-solid gel that will not run, smear, migrate or flow out onto the patient's body, requires no porous cellulose structure for support, is substantially homogeneous throughout, has a tacky surface adapted to make excellent electrical contact with the skin and to conform to surface irregularities and to flex with the movement of the body and can be applied as a coating layer onto sheet material.

These and other more detailed and specific objects of the invention will become apparent in view of the following specification and drawings which illustrate by way of example but a few of the various ways in which the present invention can be accomplished within the scope of the appended claims.

SUMMARY OF THE INVENTION

The invention provides a multipurpose medical stimulating electrode for external use in contact with the skin of a patient. The electrode is useful for cardiac pacing, TENS, neuromuscular stimulation (NMS) and other transcutaneous electrical stimulation uses. The electrode comprises an electrically conductive flexible backing having a pin socket in conductive relationship therewith. The pin socket includes a pin receptor opening for establishing electrical contact between the electrode and a flexible conductor having a metal pin terminal constructed and arranged to slide into the pin receptor opening. Attached to the backing is a semi-solid hydrogel matrix. The matrix is coated upon the backing and includes an exposed surface adapated to directly contact the skin of the patient. The matrix includes water and a natural or synthetic hydrophilic gum hydrated with water and a humectant as well as a minor amount of an ionizable gelation inhibitor in an amount sufficient to reduce the viscosity of the matrix during coating to prevent premature gelation thereof prior to application of the coating onto the backing. The ionizable gelation inhibitor has a secondary function as an electrolyte for controlling the conductivity of the matrix so as to provide a resistivity between about 1,000 and 10,000 ohm centimeters and thereby preventing current concentration and a consequent runaway condition through specific localized portions of the matrix. This avoids localized areas of high current flow through the skin. In a preferred form of the invention an electro-adhesive layer is provided around the periphery of the electrode to help bond the electrode to the skin and to seal the hydrogel matrix from the environment on all sides.

The invention will now be described by reference to the accompanying figures which illustrate by way of example a preferred form of the invention which illustrates but one of the various ways in which the invention can be accomplished within the scope of the appended claims.

THE FIGURES

DESCRIPTION OF A PREFERRED EMBODIMENT

Figure 1:
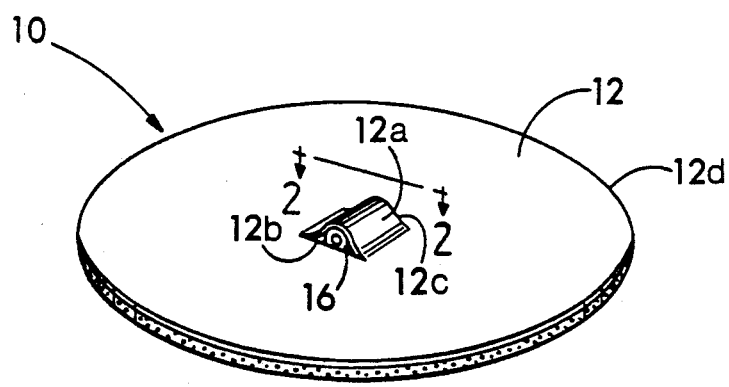
FIG. 1 is a perspective view of one preferred form of the invention.
Figure 2:
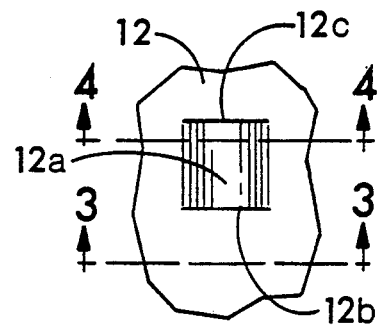
FIG. 2 is a partial plan view taken on line 2—2 of FIG. 1.
Figure 3:
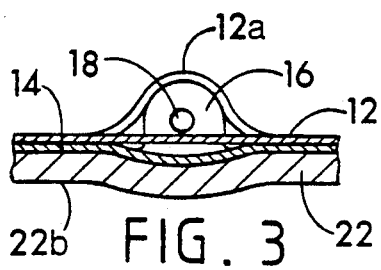
FIG. 3 is an enlarged cross-sectional view taken on line 3—3 of FIG. 2.
Figure 4:
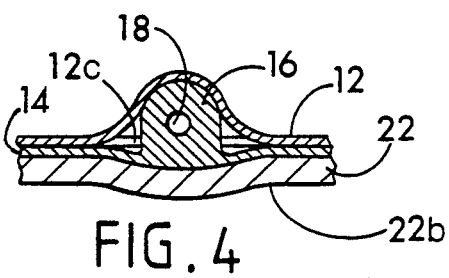
FIG. 4 is an enlarged vertical cross-sectional view taken on line 4—4 of FIG. 2.

Refer now to the figures and particulary to FIGS. 1–6 which illustrate an electrode 10 embodying the invention that in this case is circular and includes a protective nonconductive layer 12 which can be formed preferably from a sheet of plastic foam such as foamed polyurethane, polyethylene, foam rubber, etc. The protective layer 12 includes a centrally located upwardly extending tent-like projection 12a having parallel cuts 12b and 12c at each end. The tent-like projection 12a extends over and covers an upwardly extending pin socket 16 that is raised above but integral with the upper surface of an electrically conductive backing layer 14. The backing layer 14 can be formed from any suitable material such as metal foil or other electrically conductive plastic, e.g. carbon-containing silicon rubber or electrically conductive doped polyacetylene film. In this case the backing 14 comprises silicone rubber which has been rendered electrically conductive by the addition of carbon particles.

Figure 5:
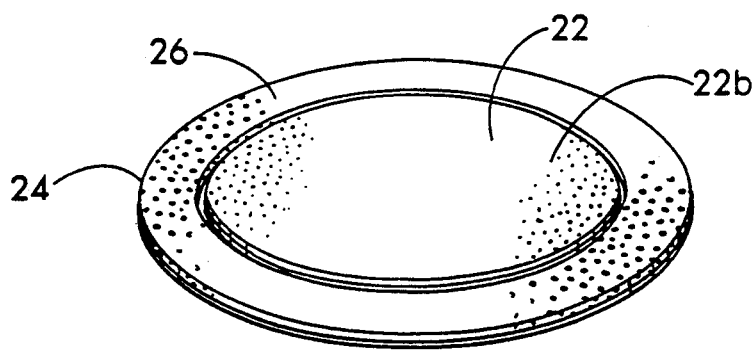
FIG. 5 is a perspective view of the electrode as seen from the underside, i.e. the skin contacting surface with the protective slip sheet or cover sheet removed.
Figure 6:
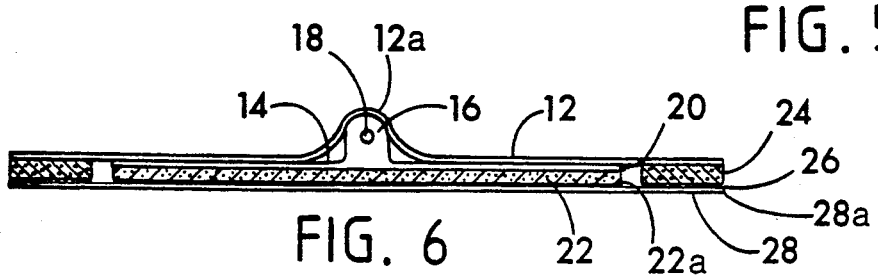
FIG. 6 is a vertical cross-sectional view of the electrode.

The pin socket 16 is provided with a centrally located horizontally extending aperture 18 which serves as a pin receptor opening for a male contact or terminal to be described below. While the dimensions are not critical, the pin receptor opening has a diameter of about 0.08 inches. The protective foam layer 12 is secured to the conductive layer 14 by means of a suitable adhesive (not shown) and also bonded to a concentric ring 24 of an adhesive supporting material such as a ring of plastic foam, e.g. polyethylene foam in this case of 0.064 inches in thickness that has a pressure-sensitive adhesive coating 26 applied to its exposed surface as shown in FIG. 5.

Applied to the lower surface of the conductive layer 14 is an electrically conductive hydrogel matrix composed of a hydrated synthetic or natural hydrocolloid such as a hydrated polyacrylamide or polysaccharide gum or a mixture thereof, together with a liquid hydrating agent, e.g. a polyhydric alcohol and water. The electrically conductive matrix 22 has an exposed skin-contacting surface 22b which is tacky and adapted to form good electrical contact with the skin. It is also sufficiently pliant to conform to the shape of the body contours and to flex with the body. The matrix moreover is in the form of a stable self-supporting or non-fluid gel which although flexible will not flow appreciably during storage or after being applied to the patient's skin.

The pressure-sensitive adhesive layer 26 completely surrounds the periphery of the electrically conductive matrix 22 and is coextensive with the edge 12d of the protective layer 12. During storage and prior to use the pressure-sensitive layer 26 and the matrix 22 are covered with a removable slip sheet or liner 28 (FIG. 6) which is peeled off just prior to use for the purpose of exposing the pressure-sensitive adhesive 26 and the sticky exposed surface 22b of the hydrogel matrix layer 22. Thus, it can be seen that the electrically conductive backing layer 14 is positioned concentrically within the pressure-sensitive adhesive 26 and foam layer 24 so that the adhesive layer extends around the periphery of the matrix 22 to adhere the electrode more reliably to the skin and also to seal the matrix 22 from the environment on all sides.

The composition of the matrix 22 will now be described.

The matrix 22 is in this instance composed of a uniformly electrically conductive flexible hydrated hydrocolloidal mass capable of establishing electrical contact with the skin. It also possesses adhesive properties. The matrix or substrate 22 attached to the conductive layer 14 is substantially homogeneous. The matrix 22 includes a dispersed phase of about 10% to 40% of the total weight of the matrix formed from a hydrophilic synthetic polymer and/or a hydrophilic natural or synthetic gum. The matrix may include synthetic polymers such as polyacrylamide, polyacrylic acid and its salts, poly maleic anhydride, polyvinyl pyrrolidone and its salts, or a modified starch such as pregelatinized starch. Of the naturally occurring gums which may be used are gum Karaya, gum acacia, locust bean gum and other polysaccharide gums. Synthetically modified gums such as modified guar gums and celluloses are also suitable. The synthetic polymers and/or synthetic or natural gums and other polysaccharides constitute the solid hydrated dispersed phase of the matrix. A liquid phase includes a humectant comprising a polyhydric alcohol such as glycerin or triethylene glycol or a mixture thereof and water which comprises about 10% to 70% of the matrix. The polyhydric alcohol may be present in an amount between 10% to 50% of the matrix and the water may be present in an amount of approximately 1.0% to 70% by weight of the matrix. All quantities and percentages stated herein are expressed as weight percent of the total matrix.

The thickness of the finished matrix is typically from approximately 1/32 to 1/4 of an inch. When applied to the skin, body moisture as well as body salts and heat are absorbed increasing its tackiness. The bonding and elastic properties of the electrode are enhanced as it ages in contact with the skin.

The polyhydric alcohol swells the hydrophilic polymer and it is involved in hydrogen bonding and cross linking of the polymer. If too much is added the matrix is soft and mushy in nature. In contrast if too little is added the matrix is hard and dry. Triethylene glycol is a less effective hydrating substance than glycerin.

The amount of hydrophilic polysaccharide gum and/or hydrophilic synthetic polymers can be varied from 10% to 40% by weight of the matrix. This material when added builds viscosity and elasticity of the mixture. Excessive amounts cause the formulations to become too elastic or tough to be coated evenly. If too little is used the matrix may be too soft or runny.

Water is added in an amount of 10% to 70% by weight of the matrix for the dual purpose of controlling resistivity of the skin it is in contact with and swelling the hydrophilic polymers, thus increasing visco-elasticity. Too much water will make the products too soft, but greater amounts will reduce the resistivity of the skin it is in contact with. If not enough water is present in the formulation, the product may be hard and dry and thus inappropriate because it does not properly hydrate the skin.

The previously mentioned components are combined in the following manner. Triethylene glycol is first mixed with the hydrophilic polymer to assure that the polymer is wetted and the mixture is homogeneous. This mixture is then combined with the most polar liquids such as glycerin and water. This process is preferably completed by means of continuous mixing rather than by batch mixing, since the viscosity of the mixture builds up rapidly with respect to time of mixing. The liquid components are preferably chilled, e.g. to between about $-25°$ C. and $+20°$ C. This decreases the rate of viscosity increase.

If desired, a viscosity stabilizer such as $Mg(OAc)_2$ can be added to the mixture for decreasing the rate at which viscosity increases in the formulation and for adjusting the electrical conductivity of the matrix. After mixing until homogeneous, the mixture is coated onto a backing, and is then cured by heating it briefly, e.g. to about 100° F. The $Mg(OAc)_2$ serves a dual function. First, it serves as an inhibitor to prevent gelation of the matrix prior to application to a supporting sheet. It also functions as an electrolyte for modifying the conductivity of the matrix. When used alone, i.e. without other electrolytes, the $Mg(OAc)_2$ should be present in an amount from about 2% to about 12% by weight and preferably in an amount from about 6% to 9% by weight. Increasing the amount of $Mg(OAc)_2$ decreases the viscosity building rate of the hydrogel matrix during the mixing procedure just prior to the application of the coating to the backing. Too great an amount will unduly inhibit viscosity increase and too small an amount will allow the gel to thicken too quickly. Moreover, if too great an amount is used the electrical conductivity of the hydrogel matrix will become excessive, producing undesired results.

It has been found that the $Mg(OAc)_2$, when it is present in the formulation, cooperates with the chilling of the mix to increase the time available for coating the matrix. Greater amounts of $Mg(OAc)_2$ will increase the time available for coating the formulation but too much will unnecessarily increase the conductivity of the matrix which will provide a greater chance for excessive transverse current flow into localized areas of skin. The gel preferably has a minimum of electrolyte and a maximum amount of water present. It has been found by removing electrolytes other than the $Mg(OAc)_2$ and especially by avoiding salts of a strong acid or base, i.e. a strong electrolyte, that the coating of the matrix onto a backing is facilitated while at the same time avoiding excessive conductivity. While the functionality of the $Mg(OAc)_2$ is not completely understood, it is known that in solution the salt does not disassociate completely. It therefore appears that the $MgOAc^-$ ion acts initially as a cross-linking inhibitor by bonding with the suitable groups present of the natural or synthetic polymer molecules so as to initially prevent cross-linking between them.

The matrix preferably has a relatively high impedance to prevent localized current concentration in a few areas into the skin. The amount of $Mg(OAc)_2$ and/or other electrolyte present controls the impedance of the matrix. It is preferred that the resistivity of the matrix be maintained between about 1,000 and 10,000 ohm centimeters and preferably about 2,000 to 6,000 ohm centimeters. By maintaining the impedance at this level it is possible to employ the electrode for TENS, for various skeletal muscle stimulation applications and for cardiac pacing as well as preventing localized concentration of current at specific points on the skin surface which is undesirable because of the pain experienced by the patient.

Viscosity buildup is also controlled by the mixing temperature. It is preferred that when triethylene glycol and glycerin are used as humectants that they be chilled to about $-25°$ C. to about $+10°$ C. and mixed into the formulation. Typically the mix is chilled to about $-5°$ C. to about $+10°$ C. At this temperature, about one minute is allowed to coat the matrix onto a backing. The matrix should enter the coater at a temperature of about $-25°$ C. to 20° C. and preferably from about $-15°$ C. to 5° C.

Figure 7:
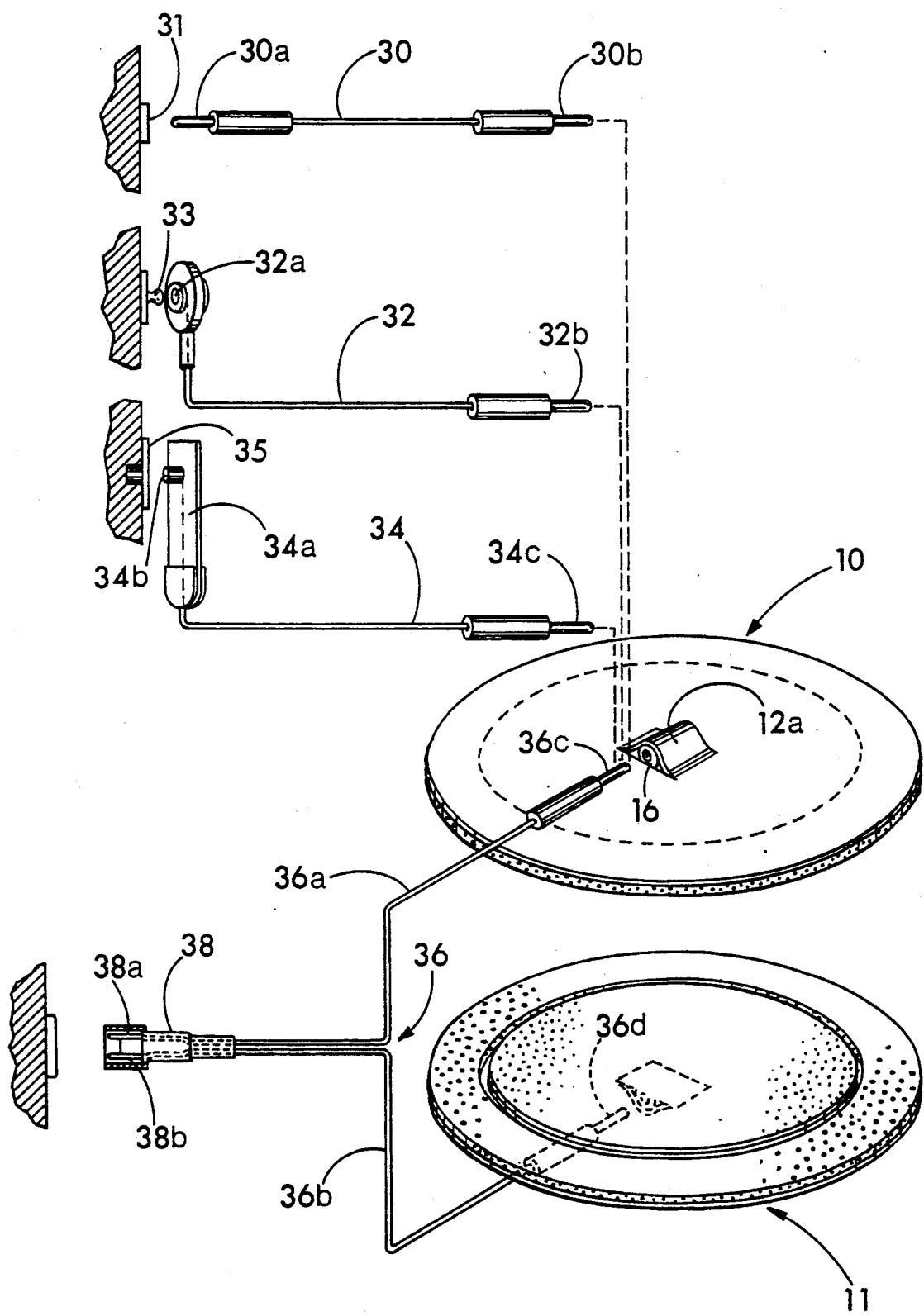
FIG. 7 is a perspective view of a pair of electrodes with insulated connecting wires and terminals.

Refer now to FIG. 7 which illustrates connectors used in conjunction with the invention. In this case two electrodes 10 and 11, both of which embody the invention, are used together. One electrode 10 serves as a stimulation electrode and the other electrode 11 serves as a grounding electrode and is adhered to the back. As shown in the figure an insulated electrical connector in the form of an insulated wire 30 is provided at opposite ends with identical pin-style male terminals or connectors 30a and 30b which typically have a diameter of about 0.080 inches. When the connector 30 is used, the terminal 30b is inserted into the opening 18 of the pin socket 16 and the terminal 30a is inserted into a female receptor of test equipment 31 sized to receive the pin 30a. The conductor 30 is a typical cable to interface the electrode 30 with a transcutaneous electrical stimulator for the heart or a neuromuscular stimulator. The stimulator provides a constant current, i.e. DC stimulation of say 50 volts at 50 mAmp. The electrode of the present invention thus provides a resistivity of between about 1,000 and 10,000 ohm centimeters under constant current conditions with a preferred range of about 2,000 to 6,000 ohm centimeters.

In FIG. 7 is also shown an electrical conductor 32 in the form of an insulated electric wire having a 0.080 inch diameter male pin connector 32b at one end and a female snap connector 32a at the opposite end that is connected during use to an electrical stimulator having a male snap connector 33 adapted to be received into the female receptor 32a. The male pin 32b is the same as 30b so that it fits the opening 18 of the electrode 10.

An electrical connector 34 comprising an insulated electric wire can also be provided. It has a male pin-style terminal 34c at one end and a male lug-style connector 34b at the other end which in this case projects from a plastic backing plate 34a. The lug 34b is adapted to fit into a socket 35 of another electrical stimulator.

An additional connector 36 is also shown. It includes a pair of electrical conductors in the form of insulated wires 36a and 36b having male pin-style connectors 36c and 36d at one end each adapted to project into an aperture 18. A connector 38 at the opposite end encloses a pair of parallel connector pins 38a and 38b which are connected respectively to the wires 36a and 36b and are adapted to form a connection with still another style of electrical stimulator. The connector 36 is a typical connector for wiring the electrode 10 to an external cardiac pacer. The pins 36c and 36d function to interface with the molded pin socket receptor of the electrode 10.

The backing 14 is relatively highly conductive compared with the matrix 22. The backing 14 when formed from a plastic resin or from rubber rendered electrically conductive, preferably has a resistivity of about 1 to 1,000 ohms/square and preferably 50 to 200, e.g. 100 ohms/square.

Typical matrix formulas are shown in the following examples.

EXAMPLE 1

|  | Optimum Weight Range as a % by weight of the Matrix | Typical |
| --- | --- | --- |
| Polyacrylamide | 10–40 | 10% |
| Triethylene Glycol | 10–50 | 15% |
| Glycerin | 10–50 | 12.5% |
| Water | 10–70 | 60% |
| Mg(OAc)$_2$ | 1–12 | 2.5% |

EXAMPLE 2

|  | Optimum Weight Range as a % by weight of the Matrix | Typical |
| --- | --- | --- |
| Polyacrylamide | 10–40 | 12% |
| Glycerin | 10–50 | 30% |
| Water | 10–70 | 55% |
| Mg(OAc)$_2$ | 1–12 | 3% |

EXAMPLE 3

|  | Optimum Weight Range as a % by weight of the Matrix | Typical |
| --- | --- | --- |
| Polyacrylamide | 10–40 | 15% |
| Triethylene Glycol | 10–50 | 20% |
| Glycerin | 10–50 | 15% |
| Water | 10–70 | 50% |

EXAMPLE 4

|  | Optimum Weight Range as a % by weight of the Matrix | Typical |
| --- | --- | --- |
| Polyacrylamide | 10–30 | 10% |
| Karaya | 5–15 | 5% |
| Triethylene Glycol | 10–50 | 15% |
| Glycerin | 10–50 | 12.5% |
| Citric Acid | 1–5 | 1.5% |
| SnCl$_2$ | .1–2 | 1.0% |
| Water | 1–70 | 60% |

EXAMPLE 5

|  | Optimum Weight Range as a % by weight of the Matrix | Typical |
| --- | --- | --- |
| Polyacrylamide | 10–40 | 5% |
| Karaya | 5–15 | 10% |
| Triethylene Glycol | 10–40 | 15% |
| Glycerin | 10–40 | 15% |
| Water | 1–70 | 55% |

Many variations of the invention within the scope of the appended claims will be apparent to those skilled in the art once the principles described above are understood.

What is claimed is:

1. A multipurpose medical stimulating electrode comprising,
    an electrically conductive backing having a resistivity on the order of about 1 to 1,000 ohm/square and an electrically conductive self-supporting hydrogel matrix coated thereupon, said matrix being adapted to make contact with the skin of a patient and being sufficiently flexible to conform to the contours of the body, said matrix comprising, a hydrophilic polymer, water in an amount of about 10% to 70% of the matrix and a humectant and said matrix
    a) being substantially free of acid or of a salt of a strong acid,
    b) having a resistivity greater than the resistivity of the backing and c) having a resistivity between about 2,000 and 10,000 ohm-centimeters to thereby reduce current concentration i localized areas and prevent a runaway condition wherein a disproportionate amount of current passes through a localized area of the skin of the patient where electrical resistance has declined for inhibiting the perception of pain by the patient and the matrix has uniformly distributed therein a gelation inhibitor in an amount sufficient to inhibit gelation of the matrix prior to forming the matrix into a coating layer.

2. The electrode of claim 1 wherein the gelation inhibitor comprises $Mg(OAc)_2$.

3. A multipurpose medical stimulation electrode for external use in contact with the skin of a patient for carrying out cardiac pacing, neuromuscular stimulation, or transcutaneous electrical stimulation comprising, an electrically conductive flexible backing, an electrically conductive pin socket in conductive relationship with the backing and extending upwardly therefrom, said pin socket having a pin receptor opening therein for establishing electrical connection between the electrode and a flexible conductor having an electrically conductive terminal constructed and arranged to slide into the pin receptor opening, a self-supporting nonfluid hydrogel matrix connected to the backing and having an exposed surface adapted to directly contact the skin of the patient and to conform to the body contours, said hydrogel comprising a hydrophilic polymer hydrated with water and a humectant and a minor amount of an ionizable gelation inhibitor in an amount sufficient to reduce the viscosity of the gel to prevent premature gelation thereof during coating of the matrix onto a support in forming said electrode, said ionizable gelation inhibitor also contributing to the electrical conductivity of the matrix and said matrix
a) being substantially free of acid or of a salt of a strong acid,
b) having a resistivity greater than the resistivity of the backing and
c) having a resistivity between about 2,000 and 6,000 ohm-centimeters to prevent current buildup through specific localized portions of the matrix, thereby avoiding a runaway condition of high current flow in localized areas of the skin for inhibiting the sensation of pain by the patient.

4. The electrode of claim 3 wherein a pressure-sensitive adhesive layer is provided to extend around the periphery of the matrix to bond the electrode to the skin and to seal the hydrogel matrix from the atmosphere on all sides.

5. The electrode of claim 3 wherein the matrix comprises a synthetic hydrocolloid comprising polyacrylamide in the amount by weight of between about 10% to about 40% water, at least one humectant in the amount by weight of about 10% to about 50%, and the gelation inhibitor is $Mg(OAc)_2$ in the amount by weight of about 1% to about 12%.

6. The electrode of claim 3 wherein the electrode comprises by weight about 10% to 40% of a natural hydrocolloid gum, about 10% to 40% by weight of polyacrylamide, an adhesive comprising vinyl acetate in the amount by weight of about 1% to 10%.

7. The electrode of claim 3 wherein the electrically conductive backing comprises a conductive silicone rubber layer having a resistivity between about 1 and 1,000 ohms/square, said pin socket comprises an integral upwardly extending projection on the upper surface of the rubber layer and said pin socket has a horizontally disposed opening therein to define said pin receptor.

8. The electrode of claim 3 wherein the matrix contains karaya gum dispersed uniformly therein in the amount of from about 10% to 40% by weight of the matrix.

9. The electrode of claim 5 in combination with a flexible electrical conductor having a male pin-style terminal at one end and a selected one of a plurality of different terminals at the other end, said pin receptor opening of the pin socket receiving said male pin-style terminal and each of said different terminals at the other end of the flexible connector being interfaced with an electrical stimulator.

10. The electrode product of claim 3 wherein said matrix is manufactured by a process characterized by coating said matrix upon a sheet of flexible supporting material while said matrix is in a chilled condition.

11. The electrode product of claim 10 wherein said matrix is manufactured by a process characterized by chilling the matrix to between about $-25°$ C. and $20°$ C. prior to being coated onto the supporting material.

12. A multipurpose medical stimulating electrode comprising,
an electrically conductive backing having a resistivity on the order of about 1 to 1,000 ohm/square and an electrically conductive self-supporting hydrogel matrix coated thereupon, said matrix being adapted to make contact with the skin of a patient and being sufficiently flexible to conform to the contours of the body, said matrix comprising, a hydrophilic polymer, water in an amount of about 10% to 70% of the matrix and a humectant and said matrix
a) being substantially free of acid or of a salt of a strong acid,
b) having a resistivity greater than the resistivity of the backing and
c) having a resistivity between about 2,000 and 10,000 ohm-centimeters to thereby reduce current concentration in localized areas and prevent a runaway condition wherein a disproportionate amount of current passes through a localized area of the skin of the patient where electrical resistance has declined for inhibiting the perception of pain by the patient and $Mg(OAC)_2$ is present in an amount sufficient to prevent premature gelation of the matrix prior to coating the matrix onto the electrically conductive backing.

* * * * *